United States Patent [19]

Landsburg

[11] Patent Number: Plant 6,977

[45] Date of Patent: Aug. 8, 1989

[54] RED MAPLE — LANDSBURG CULTIVAR

[75] Inventor: Roger B. Landsburg, Brainerd, Minn.

[73] Assignee: Bailey Nurseries, Inc., St. Paul, Minn.

[21] Appl. No.: 182,423

[22] Filed: Apr. 18, 1988

[51] Int. Cl.[4] ..... A01H 5/00

[52] U.S. Cl. ..... Plt./51

[58] Field of Search ..... Plt./51

*Primary Examiner*—Robert E. Bagwill

*Attorney, Agent, or Firm*—Burns, Doane, Swecker & Mathis

[57] ABSTRACT

A new and distinct cultivar of red maple, botanically known as *Acer rubrum* is provided. The new cultivar is distinguished from other red maples by its excellent hardiness in combination with excellent brilliant red fall coloration. The new cultivar additionally possesses a broad oval configuration, good vigor, and serves particularly well as an attractive landscape planting.

3 Drawing Sheets

SUMMARY OF THE INVENTION

The original tree of the new cultivar of *Acer rubrum* was discovered when observing its distinctive appearance while growing in a lawn adjacent a residence at 802 South Seventh Street, Brainerd, Minn. The exact origin of the tree is unknown. However, it is believed that the seed which produced the tree likely was formed on a red maple tree grown in the general vicinity of Brainerd.

Budwood was removed from the original tree in August, 1977, and was shipped to a planting area at Yamhill, Oreg. where it was budded on *Acer rubrum* seedling understock. The resulting trees were returned to Minnesota during the spring of 1980, where they were planted near St. Paul, Minn. for further study. Also, during 1981, trees of the new variety were planted for experimental study at (1) the Minnesota Landscape Arboretum at Chaska, Minn., (2) the North Dakota State University at Absareka, N.D., (3) the University of Wisconsin Arboretum at Madison, Wis., and (4) the Boerner Botanical Garden at Milwaukee, Wis. These studies have well confirmed the distinctiveness of the new cultivar.

It was found that the following combination of characteristics is exhibited by the new cultivar of *Acer rubrum:*

(a) assumes a broad oval configuration as a young tree and maintains this configuration to maturity,
(b) exhibits a vigorous growth habit,
(c) forms brilliant red foliage coloration in the fall,
(d) exhibits superior winter hardiness which is generally comparable to that of the Northwood and Morgan cultivars, and
(e) generally assumes its fall coloration earlier than other red maples.

Asexual reproduction of the new variety by budding has confirmed that the new variety can be propagated in a stable manner and that its novel combination of characteristics is reliably transmitted to succeeding generations. Tissue culture also is being used to propagate the new variety.

The new cultivar has been named Landsburg cultivar, and is being marketed by Bailey Nurseries, Inc. of St. Paul, Minn., under the Firedance trademark.

BRIEF DESCRIPTION OF THE PHOTOGRAPHS

The accompanying photographs show representative specimens of the new cultivar of *Acer rubrum* as depicted in color as true as is reasonably possible to make the same in color illustrations of this character. The specimens illustrated were observed during September at Brainerd, Minn.

DETAILED DESCRIPTION OF THE NEW CULTIVAR

Figure 1:
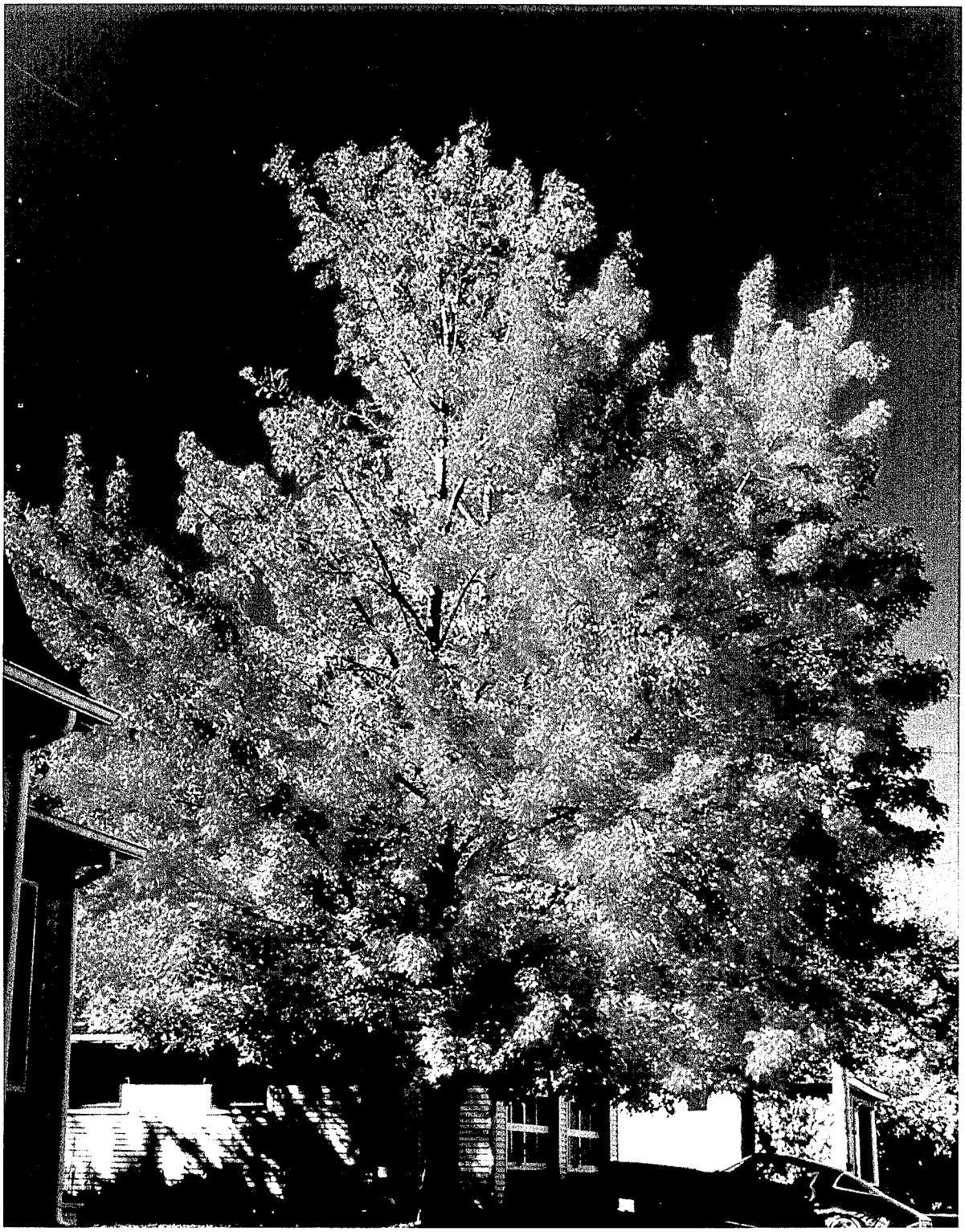
FIG. 1 illustrates the broad oval configuration and the fall leaf coloration of the original tree of the new cultivar.
Figure 2:
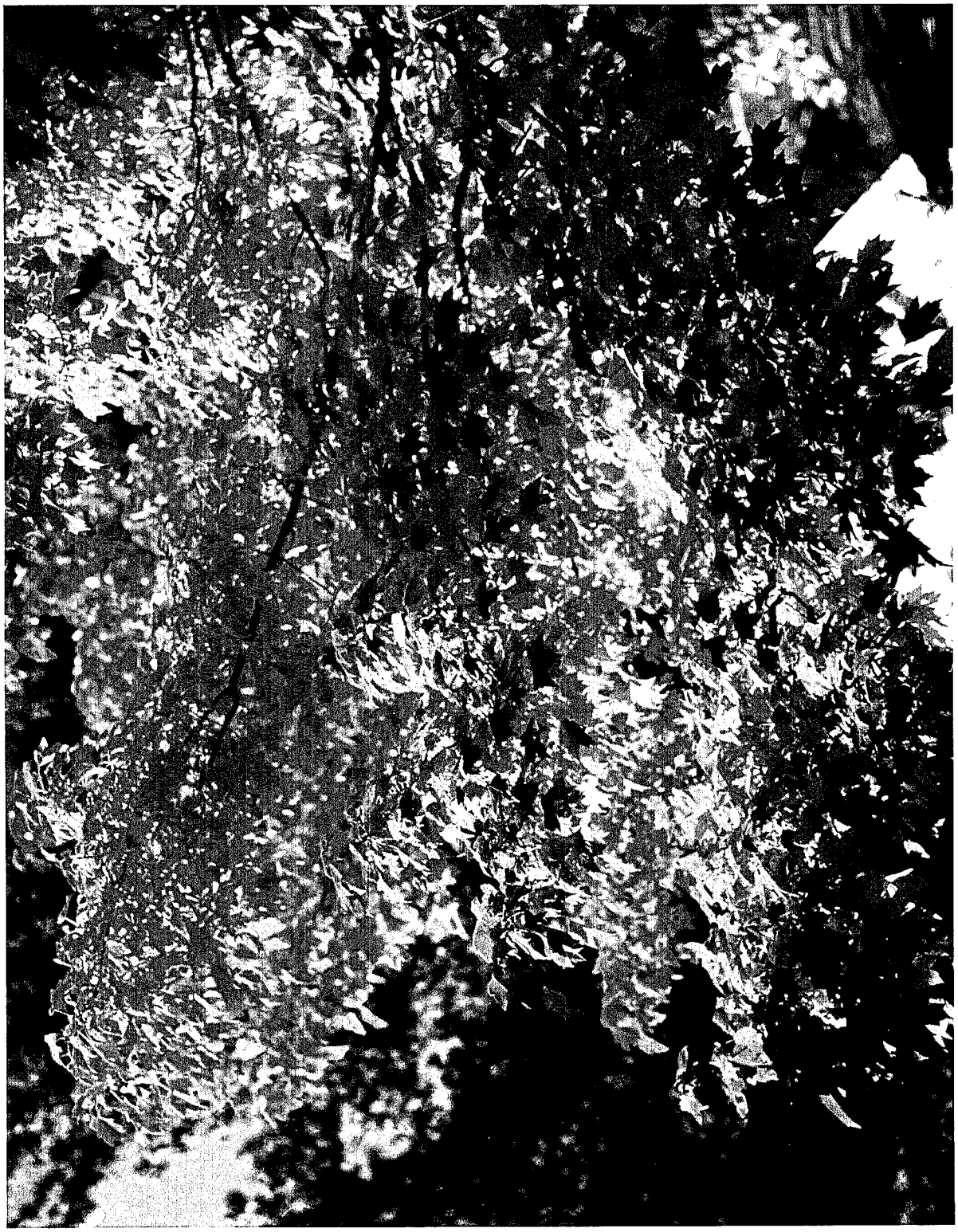
FIG. 2 illustrates a closer view of the fall foliage of the new cultivar as it appears on the lower substantially horizontal branches.
Figure 3:
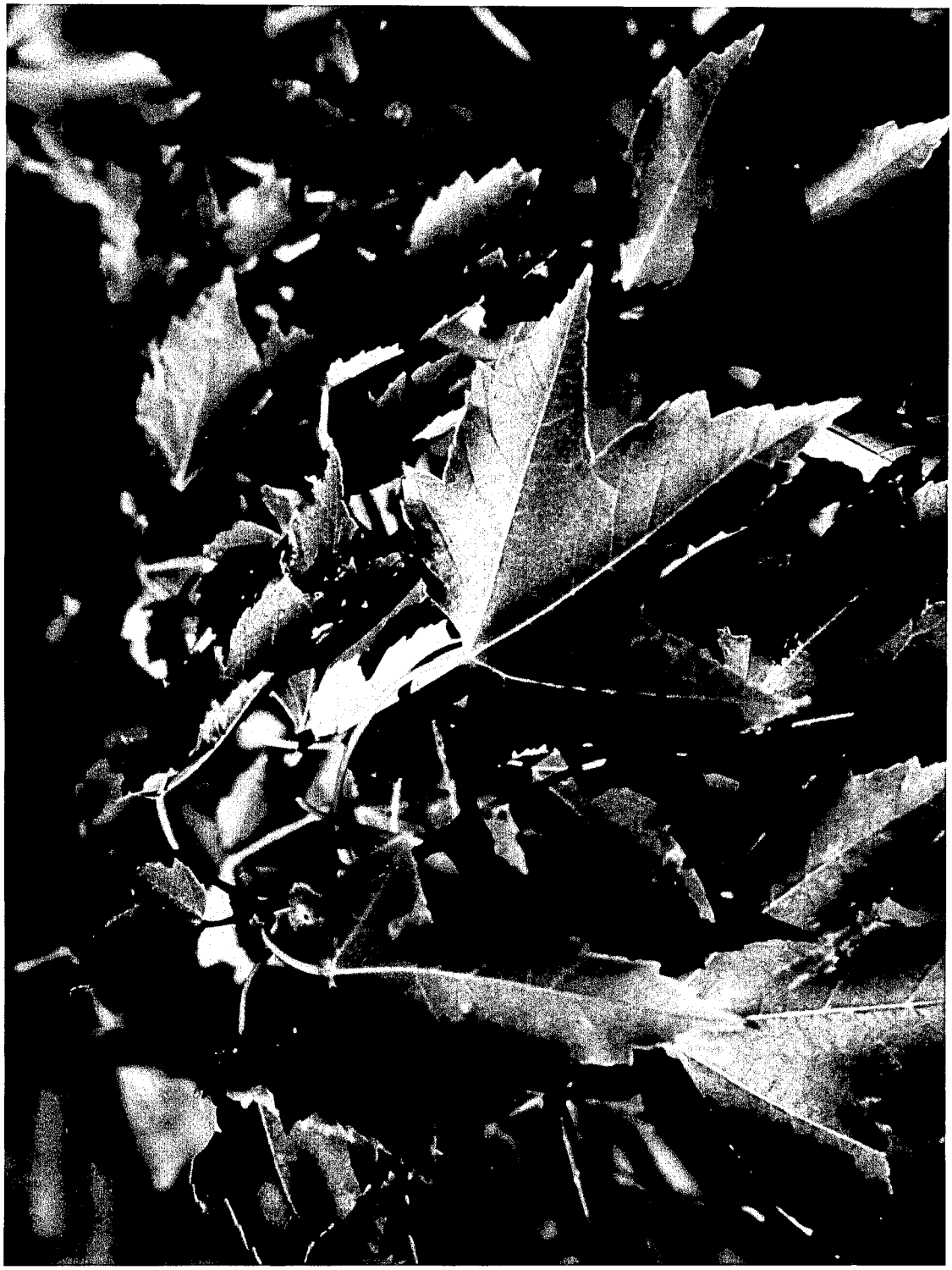
FIG. 3 illustrates the appearance of typical foliage of the new cultivar during the summer.
Figure 3:
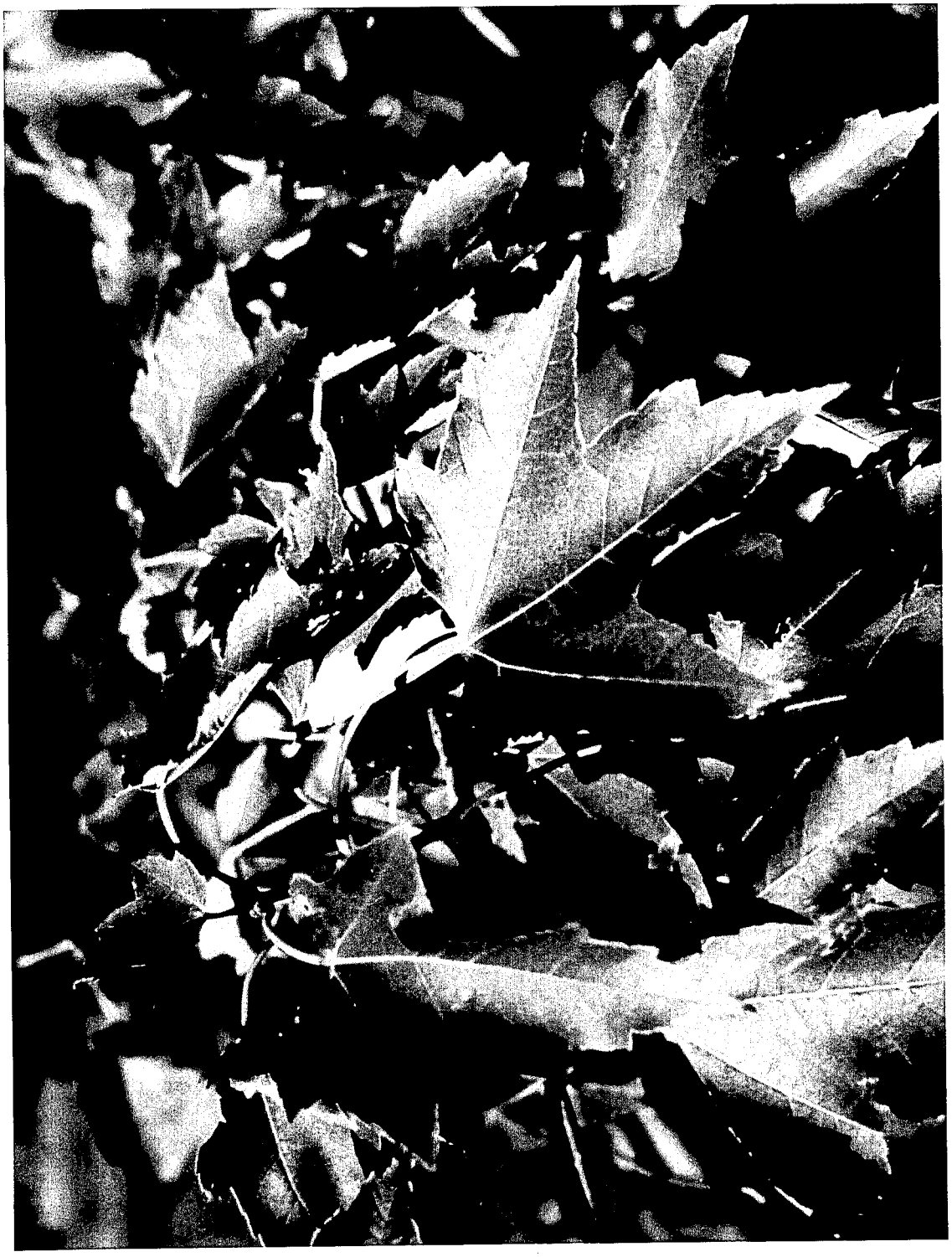

The following is a detailed description of the new cultivar of *Acer rubrum* with color terminology in accordance with the R.H.S. Colour Chart of The Royal Horticultural Society, London, England. The coloration provided in common terms is to be accorded its usual dictionary significance. The trees described were grown in Minnesota.

The new cultivar is an excellent hardy *rubrum* for use as a landscape planting particularly in those areas where superior hardiness is required. The new cultivar exhibits a good oval form (as illustrated) as well as a good branching habit. The broad oval tree configuration is exhibited as a young tree and is well maintained to maturity.

Typical leaves of the new variety commonly measure approximately 8 to 11 cm. in width and approximately 8 to 12 cm. in length. The petioles commonly measure approximately 4 to 7 cm. in length. New growth having a length of approximately 30 to 45 cm. commonly is formed per branch per growing season, and the distance between nodes commonly is approximately 8 cm. The fruit commonly is approximately 2 to 2.5 cm. in length per one-seeded samara.

The brilliant red fall coloration has been demonstrated to be outstanding at all of the test locations previously identified. Such coloration has been as good as or better than that of the other cultivars adapted to be grown at these sites, and is markedly superior to that of the Northwood cultivar.

The brilliant red fall coloration of the new variety tends to be of a deeper red in those leaf areas which are most exposed to sunlight. For instance, such fall coloration commonly tends to vary between Red Group 41A, Red Group 43B, and Red Group 44B depending upon degree of exposure of the leaves to sunlight.

Such fall coloration tends to form on the foliage of the new cultivar earlier than that of other *Acer rubrum* cultivars. For instance, at Brainerd, Minn., the new cultivar commonly tends to assume its fall coloration approximately two weeks earlier than the Red Sunset, October Glory, Bowhall, Armstrong and Schlesinger cultivars. Also, at this location the new cultivar tends to assume its fall coloration approximately 5 to 7 days earlier than the Northwood cultivar.

The winter hardiness of the new variety is particularly noteworthy. It has successfully withstood temperatures as low as −40° F. and to thereby exhibit a winter hardiness which is superior to that of most other *Acer rubrum* cultivars. The winter hardiness of the new cultivar is believed to be generally comparable to that of the Northwood and Morgan cultivars which are known for their abilities to well withstand low temperatures.

The new cultivar exhibits a vigorous growth habit which is superior to that of typical *Acer rubrum* seedlings and is generally comparable to that of other *Acer rubrum* cultivars.

The leaves of the new cultivar tend to exhibit a deeper green coloration prior to the onset of fall coloration than commonly is exhibited by *Acer rubrum.* It is common for many of the leaves of the new cultivar to exhibit a concave curl. The three lobes of the leaves commonly are more acute than those exhibited by *Acer rubrum.* Also, the leaf petioles of the new cultivar commonly are a deeper red than usual.

The buds and bark of the young twigs of the new cultivar tend to be deeper in coloration than is common for a typical *Acer rubrum* seedling. For instance, the winter bud coloration typically in Greyed-Purple Group 183A, the coloration of one-year old twigs typically is Red Group 46A, and the coloration of two-year old twigs typically is Grey Group 201C.

I claim:

1. A new and distinct cultivar of *Acer rubrum* tree, characterized particularly as to novelty by the following combination of characteristics:

(a) assumes a broad oval configuration as a young tree and maintains this configuration to maturity,
(b) exhibits a vigorous growth habit,
(c) forms brilliant red foliage coloration in the fall,
(d) exhibits superior winter hardiness which is generally comparable to that of the Northwood and Morgan cultivars, and
(e) generally assumes its fall coloration earlier than other red maples, substantially as illustrated and described.

* * * * *